(12) United States Patent
Hongou

(10) Patent No.: US 8,932,222 B2
(45) Date of Patent: Jan. 13, 2015

(54) ULTRASONIC DIAGNOSTIC APPARATUS AND ULTRASONIC DIAGNOSTIC APPARATUS AND SYSTEM USING AN ULTRASONIC PROBE

(75) Inventor: Hironobu Hongou, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1454 days.

(21) Appl. No.: 11/774,142

(22) Filed: Jul. 6, 2007

(65) Prior Publication Data

US 2008/0015437 A1    Jan. 17, 2008

(30) Foreign Application Priority Data

Jul. 13, 2006  (JP) ................. 2006-193086

(51) Int. Cl.
- *A61B 8/00* (2006.01)
- *A61B 8/14* (2006.01)
- *G01S 7/52* (2006.01)
- *G01S 15/89* (2006.01)
- *A61B 8/06* (2006.01)
- *A61B 8/08* (2006.01)

(52) U.S. Cl.
CPC ... *A61B 8/14* (2013.01); *A61B 8/54* (2013.01); *A61B 8/546* (2013.01); *G01S 7/5208* (2013.01); *G01S 15/8925* (2013.01); *G01S 15/8927* (2013.01); *A61B 8/06* (2013.01); *A61B 8/08* (2013.01); *A61B 8/0883* (2013.01); *A61B 8/488* (2013.01)
USPC ......................... 600/437; 800/459

(58) Field of Classification Search
CPC .............................. G01S 15/8929; A61B 8/14
USPC ......... 600/437, 440, 441, 443, 447, 453, 455, 600/459, 472; 367/94, 105
See application file for complete search history.

(56) References Cited

U.S. PATENT DOCUMENTS

| | | | |
|---|---|---|---|
| 4,598,589 A | 7/1986 | Riley et al. | |
| 5,562,097 A | 10/1996 | Yao | |
| 6,752,761 B2 * | 6/2004 | Amemiya | 600/437 |
| 6,795,374 B2 * | 9/2004 | Barnes et al. | 367/138 |
| 2005/0096546 A1 * | 5/2005 | Hazard et al. | 600/447 |

FOREIGN PATENT DOCUMENTS

JP     2000-139907     5/2000

* cited by examiner

*Primary Examiner* — Rajeev Siripurapu
(74) *Attorney, Agent, or Firm* — Oblon, Spivak, McClelland, Maier & Neustadt, L.L.P.

(57) ABSTRACT

An ultrasonic diagnostic apparatus has an ultrasonic probe for transmitting and receiving an ultrasonic wave at a group of a plurality of ultrasonic vibrators arranged in an array form to and from a subject and incorporating a preamplifier groups for amplifying the resulting weak ultrasonic echo received after obtaining tissue information about the subject. The ultrasonic vibrator group has a first area to which a first amplifier group is to be connected and a second preamplifier group to which a second amplifier group is to be connected. In an operating mode to cease the first preamplifier group from operating, a control circuit switches to supply the bias current being supplied to the first preamplifier group over to the second preamplifier group.

13 Claims, 7 Drawing Sheets

ULTRASONIC DIAGNOSTIC APPARATUS AND ULTRASONIC DIAGNOSTIC APPARATUS AND SYSTEM USING AN ULTRASONIC PROBE

CROSS-REFERENCE TO RELATED APPLICATIONS

This application is based upon and claims the benefit of priority from prior Japanese Patent Application No. 2006-193086, filed Jul. 13, 2006, the entire contents of which are incorporated herein by reference.

BACKGROUND OF THE INVENTION

1. Field of the Invention

The present invention relates to a real-time ultrasonic diagnostic apparatus and ultrasonic diagnostic apparatus and system using an ultrasonic probe that is to obtain in real time an image in a living body while scanning with an ultrasonic beam, and more particularly to an ultrasonic diagnostic apparatus using a probe incorporating an electronic circuit therein.

2. Description of the Related Art

Recently, the ultrasonic two-dimensional (2D) array probe, etc. tend to incorporate an electronic circuit in the probe head thereof, to generate a transmission waveform and amplify/partially beam-form the resulting reception echo. For example, JP-A-2000-139907 describes an ultrasonic diagnostic apparatus using such a two-dimensional array probe.

Meanwhile, it can be considered to use a stack of piezoelectric elements, etc. in order to suppress the impedance increase resulting from the miniaturization of vibrator elements.

For example, in the real-time ultrasonic diagnostic apparatus using a probe incorporating an electronic circuit, its probe handle is made up with an ultrasonic vibrator group, a pulser group, a preamplifier group, a sub-array beam former group, and a control circuit for controlling those. Meanwhile, an ultrasonic probe is constituted by the probe handle together with a probe cable, a probe connector and an electronic circuit group and an in-probe-connector control circuit.

Meanwhile, in the ultrasonic diagnostic apparatus body to which the ultrasonic probe is connected through the probe connector, amplification is made on the ultrasonic echo signals subjected to reception-delay addition at the in-body amplifier group. The amplified ultrasonic echo signals are matched in timing together at a reception-delay addition circuit and then detected at a signal processing section, to be extracted of an envelope. This is transformed in coordinate at the image processing section and processed suitably for image display, thus being displayed on a display section. This allows for displaying the subject as shape information in a real time.

In the meanwhile, by transmitting and receiving an ultrasonic wave at a center frequency f0 to and from the blood flowing through the subject, an ultrasonic beam having a frequency f0+fd is received by means of the moving corpuscles through the action of a Doppler shift fd proportional to the blood velocity. For this reason, by detecting the Doppler shift frequency fd and displaying a change in time thereof, blood-velocity information is to be displayed as a Doppler image.

In such a case, by two-dimensionally mapping the detected Doppler shift frequencies fd and displaying those over the ultrasonic image through proper color change, the image of the subject can be displayed in real time as a color Doppler image (not shown) including blood velocity information.

The ultrasonic probe recently uses a two-dimensional array of vibrators wherein the number of vibrators amounts to several thousands while reduced in their individual sizes. In such a case, if connecting the probe directly to the ultrasonic diagnostic apparatus, there is a need of increasing number of cables. This however increases cable thickness and hence raises troublesomeness upon handling. Moreover, there encounters a difficulty in delivering a drive waveform to the precise vibrators with efficiency and in conveying an ultrasonic echo, received at the precise vibrators, with quality.

Consequently, for two-dimensional array or the like, the ultrasonic probe is mounted with an electronic circuit including transmission and reception circuits. In addition, it is an often practice to reduce the number of input signal lines to the ultrasonic diagnostic apparatus by driving a number of precise vibrators with easiness and efficiency, amplifying a received weak ultrasonic echo with efficiency and summing up the values through partial reception-beam forming as to several vibrators a time.

Figure 1:
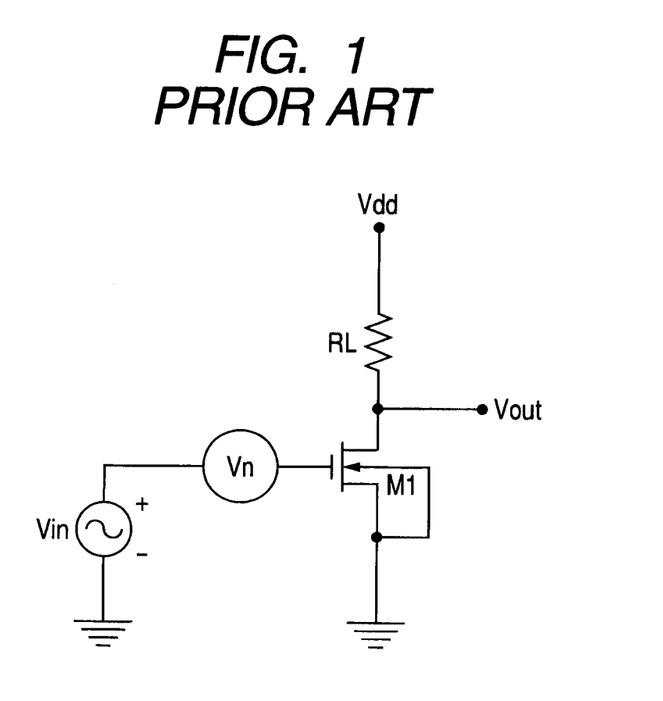
FIG. 1 is a view explaining the relationship between a bias current to the ultrasonic-echo amplifying FET and a noise, in the prior art.

However, there is a need to reduce the heat generation at the electronic circuit incorporated in the probe, in order to suppress the temperature rise of the ultrasonic probe within a permissible level. Consequently, there is a problem that the power, to be supplied to the incorporated electronic circuit, could not be increased. Meanwhile, as for the preamplifier group for ultrasonic-echo amplification, FETs (field-effect transistors) in most cases are used as representative amplification elements. The FET preamplifier requires a greater amount of bias current as shown in FIG. 1, in order to obtain a broad dynamic range at low noise.

The FET M1 has a noise-in-input (thermal noise) that is to be determined as in the following.

$$v_n = 4kT(2/3) \cdot (1/gm)$$

$$gm = 2 \cdot I_D / (VGS - V_{TH})$$

Accordingly, the bias-current must be increased for reducing the noise.

Namely, in order to amplify an extremely weak Doppler signal superposed on a great-amplitude clutter (reflection of from heart wall, etc.) as in a continuous wave Doppler (SCW) mode, there is a need to supply a significantly great bias current that is nearly double the bias current for obtaining the usual B-mode image.

As a result, heat generation increases on the preamplifiers to increase the probe temperature, thus resulting in excessive heat generation and possible improper operation of the incorporated electronic circuit. In case the bias current is used suppressively in order to avoid it, dynamic range is not fully obtained as to the preamplifiers. This makes it difficult to amplify a weak signal component with fidelity, thus making it impossible to obtain information to a diagnostically required extent.

BRIEF SUMMARY OF THE INVENTION

Therefore, it is an object to provide an ultrasonic diagnostic apparatus and an ultrasonic diagnostic apparatus and system using an ultrasonic probe that are reduced in noise level at the preamplifiers without increasing consumption power and heat generation but increased in dynamic range thereby securing the reception performance in a continuous wave Doppler mode, etc. and obtaining a good ultrasonic image, wherein the ultrasonic diagnostic apparatus uses a two-dimensional array probe, etc. incorporating an electronic circuit such as preamplifiers.

Namely, the first invention comprises:

an ultrasonic probe that has a plurality of ultrasonic vibrators arranged in an array form and for transmitting and receiving an ultrasonic wave to and from a subject, and a plurality of preamplifiers connected respectively to the plurality of ultrasonic vibrators and for amplifying a reception signal obtained by transmission and reception thereof;

a transmission/reception control section that is configured to transmit and receive, by switchover, a pulse wave and a continuous wave at the ultrasonic probe; and a control circuit that controls to supply a bias current substantially equivalently to the plurality of preamplifiers when sending/receiving a pulse wave, and to supply a bias current greater than a bias current, to be supplied to the preamplifiers to be connected to the ultrasonic vibrators for use in transmission, to the preamplifiers to be connected to the ultrasonic vibrators for use in reception when sending/receiving a continuous wave.

Meanwhile, the second invention comprises:

a plurality of ultrasonic vibrators that are arranged in an array form to transmit and receive an ultrasonic wave to and from a subject and having a first area and a second area;

a pulser group that drives the plurality of ultrasonic vibrators at the first and second areas and causes to transmit an ultrasonic wave;

a preamplifier group that amplifies tissue information about the subject received by the plurality of ultrasonic vibrators at the first and second areas; and a control circuit that, in an operating mode to cease from operating a first preamplifier group to be connected to the first area and from operating a second pulser group to be connected to the second area, control is made to supply a bias current, being supplied to the first preamplifier group, to a second preamplifier group to be connected to the second area.

Furthermore, the third invention comprises:

an ultrasonic probe having a plurality of ultrasonic vibrators that are arranged in an array form to transmit and receive an ultrasonic wave to and from a subject and having a first area and a second area, a pulser group that drives the plurality of ultrasonic vibrators at the first and second areas and causes to transmit an ultrasonic wave, a first preamplifier group that amplifies tissue information about the subject received at the first area of the plurality of ultrasonic vibrators, a second preamplifier group that amplifies tissue information about the subject received at the second area of the plurality of ultrasonic vibrators, and a control circuit that controls to supply a bias current, being supplied to the first preamplifier group, to the second preamplifier group in an operating mode to cease the first preamplifier group from operating; and an ultrasonic diagnostic apparatus connected to the ultrasonic probe and for obtaining information obtained at the ultrasonic probe and supplying power.

According to the invention, there is provided an ultrasonic diagnostic apparatus and ultrasonic diagnostic apparatus and system using an ultrasonic probe, which is reduced in noise level at the preamplifiers without increasing consumption power and heat generation but increased in dynamic range thereby securing the reception performance in a continuous wave Doppler mode, etc. and obtaining a good ultrasonic image, wherein the ultrasonic diagnostic apparatus uses a two-dimensional array probe, etc. incorporating an electronic circuit such as preamplifiers.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principle of the invention.

DETAILED DESCRIPTION OF THE INVENTION

With reference to the drawings, explanation is now made below on embodiments according to the present invention.

First Embodiment

Figure 2:
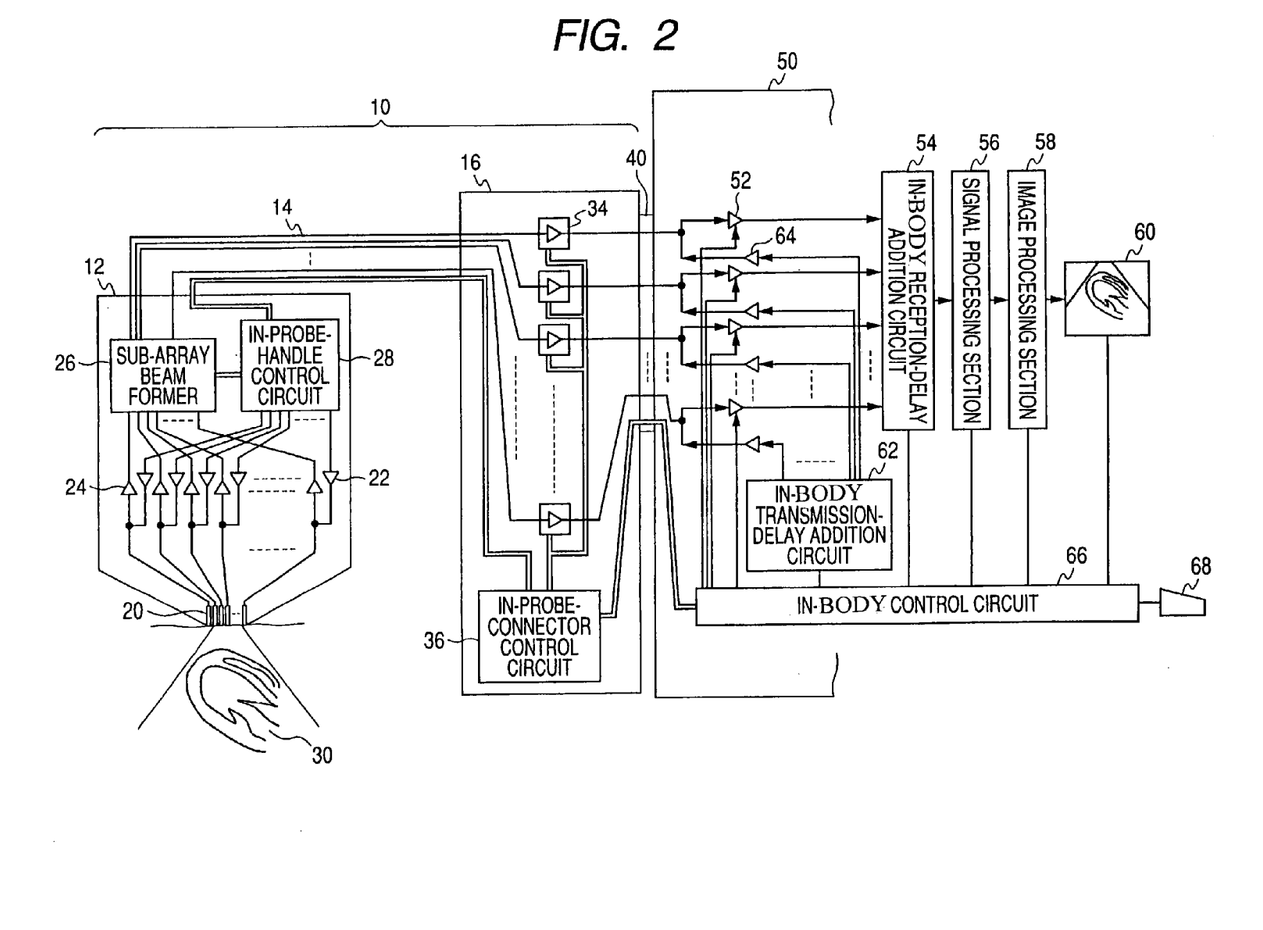
FIG. 2 is a block diagram showing a construction of a real-time ultrasonic diagnostic apparatus using a probe incorporating an electronic circuit, according to a first embodiment of the present invention.

Referring to FIG. 2, there is illustrated a block diagram showing a construction of a real-time ultrasonic diagnostic apparatus using a probe incorporating an electronic circuit, according to a first embodiment of the invention.

In FIG. 2, the ultrasonic diagnostic apparatus of this embodiment includes an ultrasonic probe 10, and an ultrasonic diagnostic apparatus body 50 to which the ultrasonic probe 10 is connected through a body-end probe connector 40.

The ultrasonic probe 10 is made up with a probe handle 12, a probe cable 14 having one end connected to the probe handle 12, and a probe connector 16 connected to the other end of the probe cable 14.

The probe handle 12 is made up with an ultrasonic vibrator group 20, a pulser group 22, a preamplifier group 24, a sub-array beam former group 26, and an in-probe-handle control circuit 28 for placing those under control.

The ultrasonic vibrator group 20 are arranged, say, in an N×M array form as referred later, to transmit and receive an ultrasonic wave to and from a subject 30 (e.g. heart). The pulser group 22 is connected to the ultrasonic vibrator group 20, to drive the ultrasonic vibrator group 20 in accordance with the different timing generated by the in-probe-handle control circuit 28, thus generating an ultrasonic beam having a predetermined directivity. Due to this, an ultrasonic beam is to be irradiated from the ultrasonic vibrator 20 to the subject 30, according to an electric signal from the pulser group 22.

The preamplifier group 24 is to perform processing such as low-noise amplification and buffering in order to favorably obtain a weak ultrasonic echo signal to be received at the ultrasonic vibrator group 20, by transmitting the ultrasonic beam from the ultrasonic vibrator group 20 in a manner to reflect upon an interface where acoustic impedance is different, e.g. boundary of textures of the subject 30 and obtain information about the structure, movement, etc. of the subject 30. The sub-array beam former group 26 is to sum up the output signals of from the preamplifier group 24 by providing a delay time based on each group of several channels, thereby reducing the number of the output signal lines of from the ultrasonic probe 10. This reduces the number of probe cables 14.

The in-probe-handle control circuit 28 is to take control the operations of the pulser group 22, the preamplifier group 24 and the sub-array beam former group 26. According to the control signal of from the in-probe-handle control circuit 28, the preamplifier group 24 is set with operating conditions, e.g. bias current, on its element-by-element basis.

The probe handle 12 and the probe connector 16 are connected together through the probe cable 14. The probe connector 16 incorporates therein an electronic circuit group 34 configured by a plurality of electronic circuits and an in-probe-connector control circuit 36. The electronic circuit group 34 is to perform additional processing, such as amplification, buffering and band adjustment, on the ultrasonic echo signal, as required. Meanwhile, the in-probe-connector control circuit 36 is to control the operation of the electronic circuit group 34, and to generate a control signal, delivered from the in-probe-handle control circuit 28, on the basis of the control signal received from the ultrasonic diagnostic apparatus body 50, referred later.

The ultrasonic diagnostic apparatus body 50 is configured with an in-body preamplifier group 52, an in-body reception-delay addition circuit 54, a signal processing section 56, an image processing section 58, a display section 60, an in-body transmission-delay circuit 62, an in-body pulser group 64, an in-body control circuit 66 and an operation panel 68.

Figure 3:
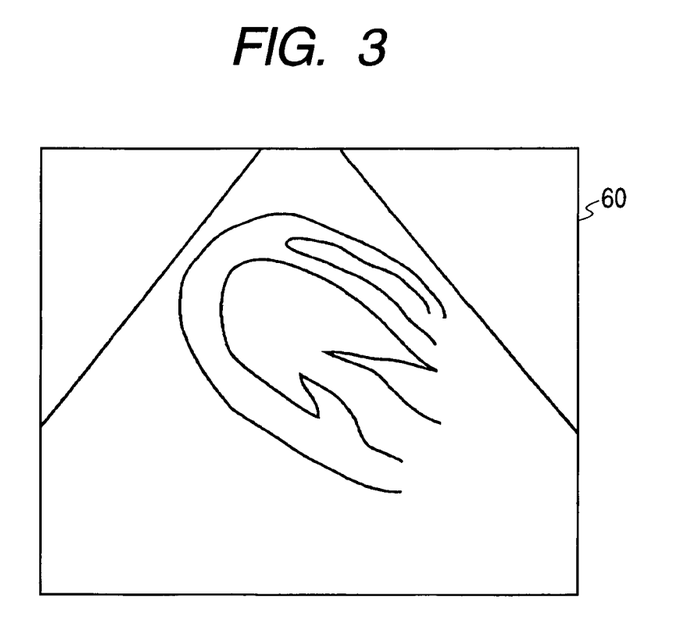
FIG. 3 is a figure exemplifying shape information about the subject-to-observe displayed in real time on a display section of the FIG. 2 ultrasonic diagnostic apparatus.

The in-body preamplifier group 52 is to amplify the ultrasonic echo signals that were first subjected to reception-delay addition at the ultrasonic probe 10 on the group-by-group basis of several channels. The ultrasonic echo signals amplified are matched in timing together by the in-body reception-delay addition circuit 54. The ultrasonic echo signals are then detected by the signal processing section 56, to extract an envelope. Furthermore, the ultrasonic echo signals, extracted of the envelope, are transformed in coordinate in accordance with a sectional plane of the subject 30 at the image processing section 58, processed in intensity level suitably for image display or so, thus being displayed on the display section 35. This allows the display section 60 to display in real time the shape information about the subject, as shown in FIG. 3.

Meanwhile, the in-body control circuit 66 is to control the operation of the processing sections in the ultrasonic diagnostic apparatus body 50 and to supply control information to the in-probe-connector control circuit 36 of the probe connector 16. The operation panel 68 is input means for the operator to input or select information, e.g. to execute a continuous wave Doppler (SCW) mode in which beam steering is available, as an operation mode.

Incidentally, the in-body transmission-delay circuit 62 and the in-body pulser group 64 are to be operated where the ultrasonic probe does not incorporate an electronic circuit, i.e. where the usual probe is connected to drive the ultrasonic vibrators 20 by the ultrasonic diagnostic apparatus body 50. It is usually incorporated in the ultrasonic diagnostic apparatus body 50 but may be omitted to provide.

Figure 4:
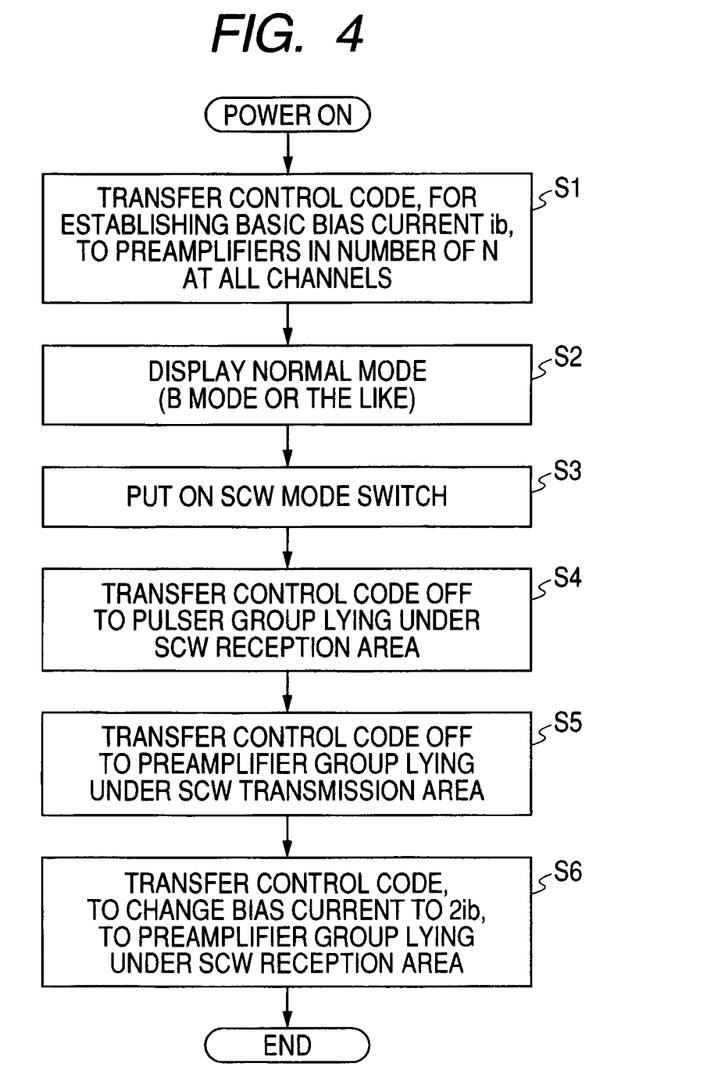
FIG. 4 is a flowchart explaining the operation of the ultrasonic diagnostic apparatus of the first embodiment of the invention.

Referring to the flowchart of FIG. 4, description is now made on the ultrasonic diagnostic apparatus according to the first embodiment of the invention.

Figure 5A:
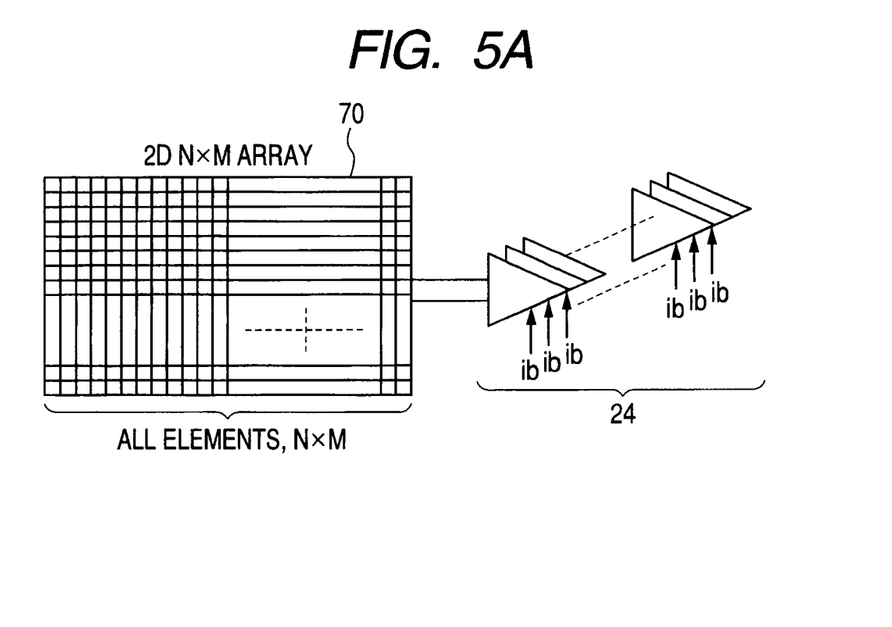
FIG. 5A is a figure explaining the ultrasonic vibrators and preamplifiers in a usual pulse transmission/reception mode.

When power is put on by means of a not-shown power supply, the present routine is started. At step S1, a control code is transferred to the preamplifier group 24 at all the channels, to establish a basic bias current ib. From the vibrator group 70 in a 2D N×M array arrangement as shown in FIG. 5A, ultrasonic echo signals amplified at the N×M preamplifier group 24 are transferred to the ultrasonic diagnostic apparatus body 50. The in-body preamplifier group 52 amplifies the ultrasonic echo signals that were first subjected to reception-delay addition at the ultrasonic probe 10 on the group-by-group basis of several channels. The ultrasonic echo signals are matched in timing at the in-body reception-delay addition circuit 54 and detected by the signal processing section 56, to extract an envelope. Then, the image processing section 58 transforms those in coordinate in accordance with a sectional plane of the subject 30 and processed in intensity level suited for image display. This allows the display section 60, at step S2, to display an image in the usual mode, e.g. B mode.

In this state, observation is assumed conducted in the SCW mode. Thereupon, at step S3, the operator is to select an SCW mode by operating the operation panel 68 of the ultrasonic diagnostic apparatus body 50. In this case, an SCW mode is selected by putting on a not-shown switch on the operation panel 68. Based on the input to the operation panel 68, the in-body control circuit 66 sets up the ultrasonic diagnostic apparatus body 50 to operate in the SCW mode. Simultaneously, a control signal is supplied to the in-probe-connector control circuit 36 of the ultrasonic probe 10. Thereupon, the in-probe-connector control circuit 36 regulates the control signal into a form to be processed by the in-probe-handle control circuit 28. Thus, the regulated control signal (control code) is conveyed to the in-probe-handle control circuit 28.

Figure 5B:
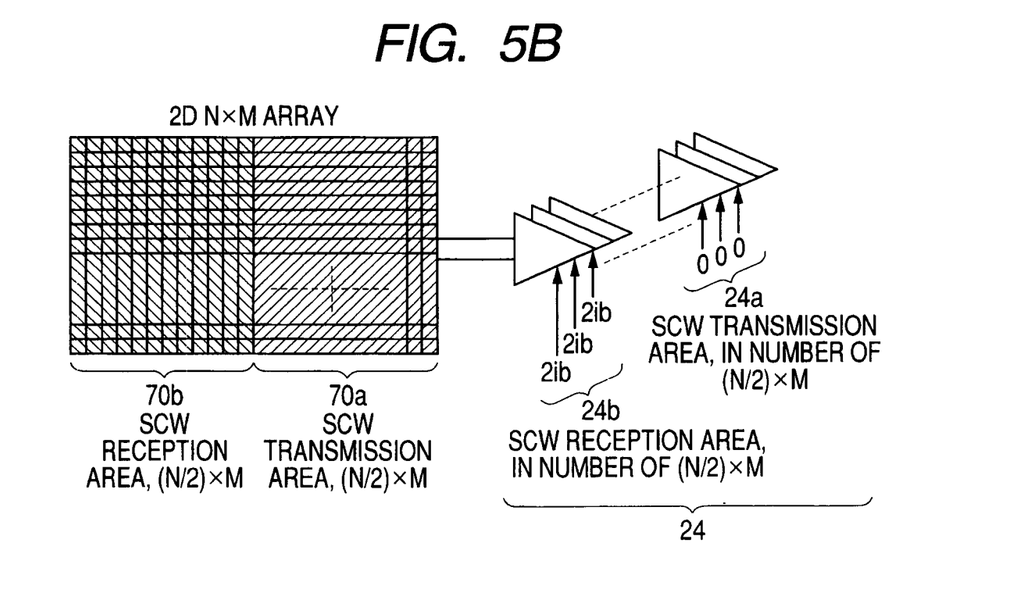
FIG. 5B is a figure explaining the ultrasonic vibrators and preamplifiers in an SWC mode.

In the in-probe-handle control circuit 28, the pulser group 22 and the preamplifier group 24 are controlled based on the control signal. This divides the 2D N×M array arrangement of vibrator group 70, into an area 70a for transmission of an ultrasonic wave and an area 70b for reception, as shown in FIG. 5B. At step S4, the in-probe-handle control circuit 28 transfers a control code to turn off the pulser group 22 lying under the SCW reception area 70b.

Furthermore, at the next step S5, the in-probe-handle control circuit 28 transfers a control code to turn off the preamplifier group 24a lying under the SCW transmission area. Then, at step S6, control is made to add the bias current ib, usually used at the preamplifier group 24a, to the bias current ib to the preamplifier 24b lying under the SCW reception area 70b as shown in FIG. 5A.

In the usual pulse transmission/reception mode, the 2D N×M array 70 serves for transmission/reception at all of its elements as shown in FIG. 5A. In such a case, the bias current to the N×M preamplifier group 24 is given ib.

In the SCW mode, the probe is used separated in region, i.e. a region for transmission and a region for reception. Namely, division is as an (N/2)×M array (SCW transmission area) 70a and an (N/2)×M array (SCW reception area) 70a, as shown in FIG. 5B. For this reason, the preamplifier group 24 is turned off (bias current rendered 0) at its (N/2)×M elements in a region to be connected to the SCW transmission area 70. The bias current (ib), being supplied to the preamplifier group 24a lying under the SCW transmission area, is added to the bias current to the preamplifier group 24b lying under the SCW reception area. Namely, the bias current, for the preamplifier group 24b lying under the SCW reception area, is given as ib+ib (=2ib). Thus, the bias current is increased. Incidentally, consumption power does not increase at the incorporated electronic circuit because the increase of bias current corresponds to the amount of consumption at the preamplifiers to be desirably put off.

Figure 6:
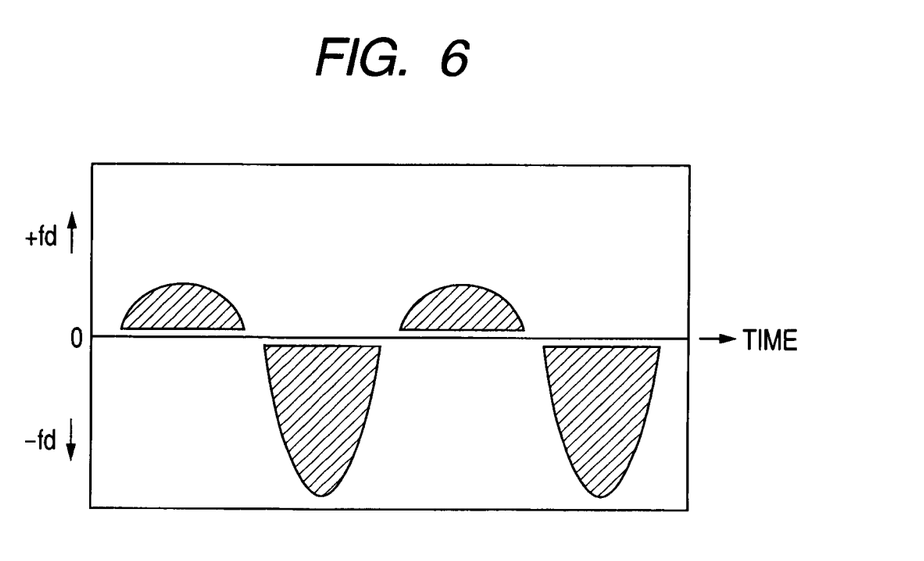
FIG. 6 is a figure exemplifying blood velocity information displayed as an SCW Doppler image.

In this embodiment, by controlling the probe-handle 12 consumption power not to exceed a predetermined value, the preamplifiers lying under the area for SCW reception can be operated to favorably amplify the extremely slight Doppler signal that is superposed on a high-amplitude clutter (reflection from the heart wall, etc.) at less noise and in an improved dynamic range without increasing the generation heat at the probe handle 12. As a result, an ultrasonic wave is transmitted at a center frequency f0 to the blood flowing through the subject. By moving blood corpuscles together with the slow movement of the heart and blood vessel walls, a weak ultrasonic echo based on the transmission beam frequency is favorably received at a frequency f0+fd experienced a Doppler shift in proportion to the blood velocity, in a state superposed on a great-amplitude clutter component resulting from the slow movement of the heart and blood cell wall, etc. By detecting the Doppler shift frequency fd and displaying the change thereof in time, blood velocity information is displayed as an SCW Doppler image as shown in FIG. 6.

Second Embodiment

Now description is made on a second embodiment according to the invention.

In the first embodiment, the ultrasonic vibrator group 20 and preamplifier group 24 were divided by on the software under control of the in-body control circuit 66, in-probe-connector control circuit 36 and in-probe-handle control circuit 28. The second embodiment is to divide the ultrasonic vibrator group 20 and preamplifier group 24 by means of hardware.

From now on, the second embodiment of the invention is described. Incidentally, the real-time ultrasonic diagnostic apparatus, using a probe incorporating an electronic circuit, is similar in configuration to that of the first embodiment. Hence, by attaching identical reference numeral to identical element to thereby omit to explain, i.e. explanation will be made only on the operation.

Figure 7:
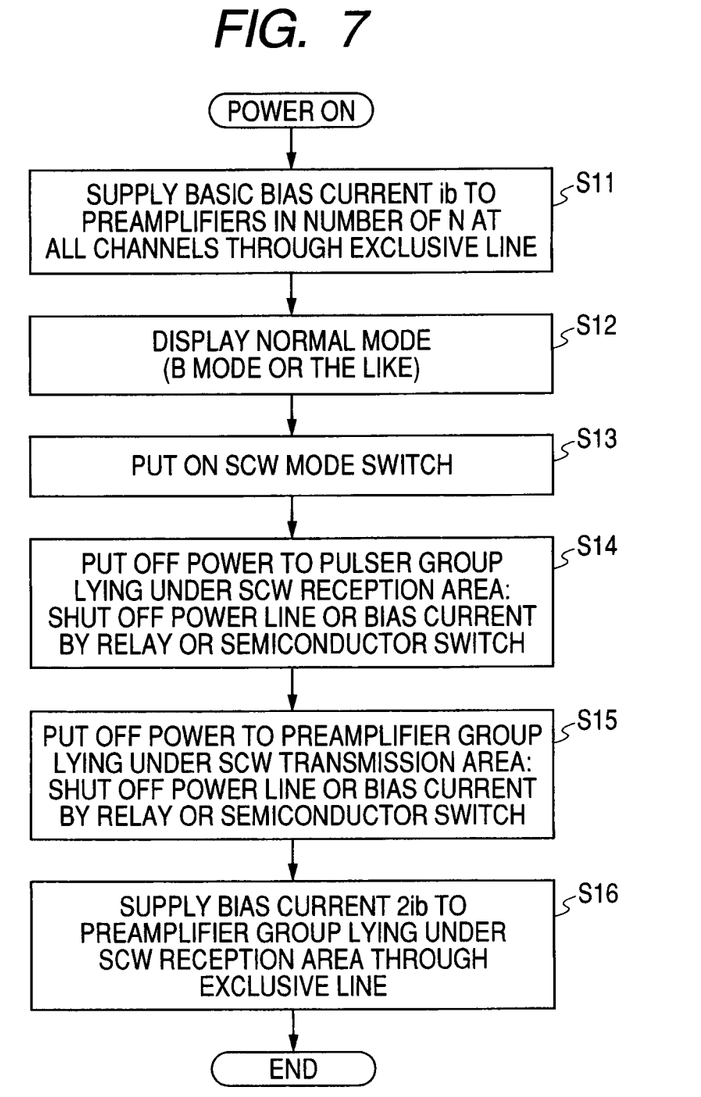
FIG. 7 is a flowchart explaining the operation of an ultrasonic diagnostic apparatus according to a second embodiment of the invention.

Referring to FIG. 7, there is illustrated a flowchart explaining the operation of the ultrasonic diagnostic apparatus, according to the second embodiment of the invention.

When putting on power by means of a not-shown power supply, the present routine is started. At step S11, a basic bias current ib is supplied through an exclusive line to the preamplifier group 24 at all the channels. Then, the in-body preamplifier group 52 amplifies the ultrasonic echo signals subjected to the first reception-delay addition on the group-by-group basis of several channels at the ultrasonic probe 10. The amplified ultrasonic echo signals are matched in timing at the in-body reception-delay addition circuit 54 and then detected at the signal processing circuit 56, to be extracted of an envelope. Then, those are transformed in coordinate matched to the sectional plane of the subject 30 at the image processing section 58 and processed in intensity level suitably for image display. This allows the display section 60, at step S12, to display an image in the usual mode, e.g. B mode.

In this state, observation is conducted at step S13 in the SCW mode. Thereupon, the operator selects an SCW mode by operating the operation panel 68 of the ultrasonic diagnostic apparatus body 50. In this case, SCW mode is selected by putting on a not-shown switch on the operation panel 68. Based on the input to the operation panel 68, the in-body control circuit 66 sets the ultrasonic diagnostic apparatus body 50 to operate in the SCW mode. Simultaneously, a control signal is supplied to the in-probe-connector control circuit 36 of the ultrasonic probe 10. Thereupon, the in-probe-connector control circuit 36 regulates the control signal into a form to be processed by the in-probe-handle control circuit 28 within the probe handle 12. The regulated control signal (control code) is supplied to the in-probe-handle control circuit 28.

Based on the control signal, the in-probe-handle control circuit 28 controls the pulse group 22 and the preamplifier group 24. This divides the 2D N×M array arrangement vibrator group 70 into an area 70a for transmission of an ultrasonic wave and an area 70b for reception, as shown in FIG. 5B. At step S14, power is turned off to the pulser group 24 lying under the SCW reception area 70b. Namely, the power line or the bias current is shut off by means of a relay or semiconductor switch provided, say, on the in-probe-handle control circuit 28.

Furthermore, at the following step S15, power is shut off to the preamplifier 24 lying under the SCW transmission area. Namely, the power line or the bias current is shut off by means of a relay or semiconductor switch provided, say, in the in-probe-handle control circuit 28. Then, at step S16, to the preamplifier group 24 is supplied a bias current 2ib in an amount double the bias current ib usually used on the exclusive line as shown in FIG. 5A.

With this structure, consumption power does not increase at the incorporated electronic circuit because the increase of bias current corresponds to the amount of consumption at the preamplifiers that are desirably to be put off.

Incidentally, in the second embodiment, the hardware was exemplified with the relay or semiconductor switch provided in the in-probe-handle control circuit 28 and for turning off the power to the pulser group 22 and preamplifier group 24. However, this is not limitative, e.g. it may be provided in the pulser group 22, the preamplifier group 24 or the like.

In the first and second embodiments, the consumption power at the preamplifier group is naturally controlled in its total amount not to exceed the upper limit thereof even if changing the ratio of transmission and reception areas at the ultrasonic vibrators.

Although the first and second embodiments described the two-dimensional array case of the ultrasonic vibrator group 20, it is not limitative. Application is similarly possible to the array vibrators arranged in a one-dimensional or irregular form.

The preamplifier group 24 is not limited to the incorporation in the probe handle 12. It can be built in the probe connector 16, in which case effects are similarly obtainable. Furthermore, SCW mode is not limitative but application is possible quite similarly as to the mode to use by separating the ultrasonic vibrator group 20 into different purposes of operating areas.

Although the invention was described by way of the embodiment, the invention is to be modified in the scope not departing from the gist thereof besides the embodiment described so far.

Furthermore, the foregoing embodiment includes various aspects of the invention, wherein various inventions are to be extracted by suitably combining a plurality of constituent elements disclosed. For example, in case certain elements are deleted from all the elements disclosed in the embodiment, the structure deleted of the elements is to be extracted as an invention where the problem mentioned in the introductory part can be solved and the effect therein can be obtained.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnostic apparatus comprising:
an ultrasonic probe that has a plurality of ultrasonic vibrators arranged in an array form and for transmitting and receiving a continuous ultrasonic wave to and from a subject, and a plurality of preamplifiers connected to the plurality of ultrasonic vibrators and for amplifying a reception signal received by the plurality of ultrasonic vibrators;
a transmission and reception control section that is configured to transmit and receive, by switchover, a pulse wave and a continuous wave at the ultrasonic probe; and
a control circuit configured to control bias currents,
wherein, in a continuous wave Doppler mode, the control is performed such that a second vibrator is used for reception and a first vibrator is used for transmission,
wherein, in a pulse wave mode, the control is performed such that a first bias current is supplied to the first vibrator and a second bias current is supplied to the second vibrator,
upon switch to the continuous wave Doppler mode from the pulse wave mode, the control is performed such that the first bias current supplied to the first vibrator is switched from the first vibrator and added to the second bias current supplied to the second vibrator.

2. An ultrasonic diagnostic apparatus according to claim 1, wherein the control circuit controls the first and second bias currents to be supplied to the plurality of preamplifiers in such a manner that a total consumption power at the plurality of preamplifiers does not exceed a predetermined upper limit value.

3. An ultrasonic diagnostic apparatus according to claim 1, wherein the ultrasonic probe is a two-dimensional array probe.

4. An ultrasonic diagnostic apparatus according to claim 1, wherein the preamplifiers are incorporated in the ultrasonic probe or in a probe connector for connecting the ultrasonic probe to a body of the ultrasonic diagnostic apparatus.

5. An ultrasonic diagnostic apparatus according to claim 1, wherein the control circuit ceases the preamplifiers in beam steering.

6. An ultrasonic diagnostic apparatus using an ultrasonic probe comprising:
a plurality of ultrasonic vibrators that are arranged in an array form to transmit and receive a continuous ultrasonic wave to and from a subject and having a first area and a second area;
a pulser group that drives the plurality of ultrasonic vibrators at the first and second areas and causes to transmit the continuous ultrasonic wave;
a plurality of preamplifiers that amplify reception signals received by the plurality of ultrasonic vibrators at the first and second areas; and
a control circuit configured to control bias currents,
wherein, in a continuous wave Doppler mode, the control is performed such that a second vibrator is used for reception and a first vibrator is used for transmission,
wherein, in a pulse wave mode, the control is performed such that a first bias current is supplied to the first vibrator and a second bias current is supplied to the second vibrator,
upon switch to the continuous wave Doppler mode from the pulse wave mode, the control is performed such that the first bias current supplied to the first vibrator is switched from the first vibrator and added to the second bias current supplied to the second vibrator.

7. An ultrasonic diagnostic apparatus using an ultrasonic probe according to claim 6, wherein the control circuit controls the first and second bias currents to be supplied to the plurality of preamplifiers in such a manner that a total consumption power does not exceed an upper limit value thereof even in case changing a ratio of first and second areas as to the first and second ultrasonic vibrators.

8. An ultrasonic diagnostic apparatus using an ultrasonic probe according to claim 6, wherein the control circuit ceases the preamplifiers in beam steering.

9. An ultrasonic diagnostic system comprising:
an ultrasonic probe having
a plurality of ultrasonic vibrators that are arranged in an array form to transmit and receive an ultrasonic wave to and from a subject and having a first area and a second area,
a pulser group that drives the plurality of ultrasonic vibrators at the first and second areas and causes to transmit a continuous ultrasonic wave,
a first preamplifier group that amplifies a reception signal received at the first area of the plurality of ultrasonic vibrators,
a second preamplifier group that amplifies a reception signal received at the second area of the plurality of ultrasonic vibrators, and
a control circuit configured to control bias currents,
wherein, in a continuous wave Doppler mode, the control is performed such that a second vibrator is used for reception and a first vibrator is used for transmission,
wherein, in a pulse wave mode, the control is performed such that a first bias current is supplied to the first vibrator and a second bias current is supplied to the second vibrator,
upon switch to the continuous wave Doppler mode from the pulse wave mode, the control is performed such that the first bias current supplied to the first vibrator is switched from the first vibrator and added to the second bias current supplied to the second vibrator; and
an ultrasonic diagnostic apparatus connected to the ultrasonic probe and for obtaining information obtained at the ultrasonic probe and supplying power.

10. An ultrasonic diagnostic system according to claim 9, wherein the control circuit controls the first and second bias currents to be supplied to the first and second preamplifier groups in such a manner that a total consumption power at the first and second preamplifier groups does not exceed an upper limit value thereof even in case changing a ratio of the first and second areas of the plurality of ultrasonic vibrators.

11. An ultrasonic diagnostic system according to claim 9, wherein the ultrasonic probe is a two-dimensional array probe.

12. An ultrasonic diagnostic system according to claim 9, wherein the first and second preamplifier groups are incorporated in the ultrasonic probe or in a probe connector for connecting the ultrasonic probe to the ultrasonic diagnostic apparatus.

13. An ultrasonic diagnostic system according to claim 9, wherein a continuous wave Doppler mode is applicable as the operating mode to cease the first preamplifier group from operating, beam steering being available in the continuous wave Doppler mode.

* * * * *